(12) United States Patent
Atherton

(10) Patent No.: US 10,271,994 B2
(45) Date of Patent: Apr. 30, 2019

(54) PASSIVE NOISE CANCELING DEVICE

(71) Applicant: Mark Atherton, Uxbridge Middlesex (GB)

(72) Inventor: Mark Atherton, Uxbridge Middlesex (GB)

(73) Assignee: Brunel University London, Uxbridge Middlesex (GB)

( * ) Notice: Subject to any disclaimer, the term of this patent is extended or adjusted under 35 U.S.C. 154(b) by 588 days.

(21) Appl. No.: 15/005,536

(22) Filed: Jan. 25, 2016

(65) Prior Publication Data

US 2017/0020735 A1    Jan. 26, 2017

Related U.S. Application Data

(63) Continuation of application No. PCT/GB2014/052198, filed on Jul. 18, 2014.

(51) Int. Cl.
*A61F 11/08* (2006.01)
*G10K 11/22* (2006.01)
*G10K 11/172* (2006.01)

(52) U.S. Cl.
CPC ............ *A61F 11/08* (2013.01); *G10K 11/172* (2013.01); *G10K 11/22* (2013.01); *A61F 2011/085* (2013.01)

(58) Field of Classification Search
CPC .. A61F 11/08; A61F 2011/085; G10K 11/172; G10K 11/22

USPC ......................................................... 181/135
See application file for complete search history.

(56) References Cited

U.S. PATENT DOCUMENTS

| | | | |
|---|---|---|---|
| 4,441,576 A | 4/1984 | Allen | |
| 5,832,094 A * | 11/1998 | Le Her | A61F 11/08 381/328 |
| 7,182,087 B1 * | 2/2007 | Marsh | A61F 11/08 128/864 |
| 7,740,104 B1 * | 6/2010 | Parkins | A61F 11/08 181/128 |
| 2006/0042867 A1 * | 3/2006 | Haussmann | A61F 11/08 181/135 |

OTHER PUBLICATIONS

International Preliminary Report on Patentability dated Nov. 19, 2015 in connection with International Application PCT/GB2014/052198.

* cited by examiner

*Primary Examiner* — Forrest M Phillips
(74) *Attorney, Agent, or Firm* — Corridor Law Group, P.C.

(57) ABSTRACT

A device for use by a dental patient fits in the patient's ear and has at least one curved resonator tube to reduce the perceived volume of a dental drill. The device can have multiple layers of resonator tubes and a port into which recorded music can be played to calm the patient further.

14 Claims, 8 Drawing Sheets

PASSIVE NOISE CANCELING DEVICE

CROSS-REFERENCE TO RELATED APPLICATIONS

This application is a continuation of International Application PCT/GB2014/052198 having a filing date of Jul. 18, 2914, entitled "Passive Noise Cancelling Device", which is related to and claims priority benefits from UK patent application No. 1313187.5 filed on Jul. 24, 2013. This application also claims foreign priority benefits from the 1313187.5 application. The '198 international application is hereby incorporated by reference herein in its entirety.

FIELD OF THE INVENTION

The present invention relates to a device for use by a dental patient to reduce the perceived sound volume of a dental drill, and in particular to a passive device which can optionally allow the user to continue to hear a personal music player and/or to communicate with the dentist.

BACKGROUND OF THE INVENTION

For many, a visit to the dentist is an anxiety-inducing affair, and the noise of the dental drill is a significant cause of this anxiety. Accordingly, a device which can reduce the perceived sound volume of the drill is also likely to be useful in reducing levels of anxiety. Ideally, such a device will also allow the patient to be able to listen to their own music (for example played on an MP3 player) and/or continue to communicate with the dentist. Conventional noise-cancelling headphones are designed to deal with noise frequencies well below 1 kHz, such as that experienced inside aircraft cabins. Dental drills rotate at speeds reaching beyond 200,000 rpm, and produce noise peak frequencies in the region of 3-6 kHz that are of relatively high power and hence very distinctive. Passive ear defenders work well in reducing sound amplitude at such high frequencies, but they do not effectively address the issue of simultaneously maintaining communication between the dentist and the patient. The simultaneous provision of noise suppression and communication requires a more sophisticated system. EP 0933007 A1 (Syracuse University) discloses an ear muffler device comprising a pair of muffler tubes in the form of headphones. The muffler tubes are configured to isolate the ear canal from ambient air and to reduce the acoustic impedance at the entrance of the ear canal across a wide range of frequencies. However, the device is bulky and looks uncomfortable and unattractive to wear.

US 2006/0042867 A1 (Haussmann et al.) discloses a hearing protection ear plug to be worn in the ear canal having an acoustic filter element and a resonance cavity which is individually designed for the acoustic requirements of the user. Accordingly, such a device would be impracticable as a mass-manufactured item for use by a plurality of users. U.S. Pat. No. 4,437,538 A1 (Ohlsson et al.) discloses an ear cap which includes a cushion formed of an elastic and porous material in combination with a perforated disk defining a cavity to attenuate the sound passing through the device.

A number of active (electronic) noise cancelling devices are disclosed in WO 02/100287 A2 (Zilberman et al.) and US 2009/0010447 A1 (Waite et al.).

There is a need for a noise cancelling device which is smaller in size than prior art devices, passive (and therefore easy and inexpensive to operate) and which can optionally allow the user to continue to listen to a personal music player and/to the dentist. It will be appreciated that such a device would have noise cancelling uses which go beyond those of a dental patient.

SUMMARY OF THE INVENTION

In accordance with a first aspect of the invention, there is provided a device for use by a dental patient to reduce the perceived sound volume of a dental drill, which device comprises a body having a first port for communication with the external auditory canal of the patient's ear, a vent for communication with the external environment, a first channel connecting the first port and the vent, at least one resonator tube having a first end and a second end, wherein the first end is proximate to and in communication with the first channel and the second end is closed, and wherein the resonator tube is curved along at least part of its longitudinal axis in order to reduce the length of a straight line from the first end to the second end.

The provision of a curved resonator tube enables the device to be provided in a compact form, while retaining its noise cancelling properties. In a preferred embodiment, the device comprises a plurality of resonator tubes and ideally each of the resonator tubes is curved as defined above. The provision of the plurality of tubes enables the noise cancelling effect of the device to be maximized, or at least increased, while retaining the compact form.

The device can include a set of resonator tubes which are disposed in the same plane (in other words, a layer of tubes) and the plane is preferably normal to the longitudinal axis of the channel. The provision of a set of tubes enables a plurality of tubes to be provided in a particularly compact form.

In a preferred embodiment, the device comprises a plurality of sets, more preferably from two to five sets and most preferably three sets of resonator tubes. It has been discovered that the provision of a plurality of sets results in a device which is particularly effective at cancelling noise, with two layers being better than one and three layers being better than two.

The number of resonator tubes in each set can range independently from three to five, and preferably each set has the same number of resonator tubes. In a preferred embodiment, at least two of the resonator tubes can have the same length as each other, and there can be a plurality of pairs of resonator tubes of the same length within the set. Without wishing to be constrained by theory, it is thought that use of matched tubes that cancel out specific frequencies of sound can have a particularly effective noise cancelling effect. Also, the use of tubes of different lengths within the device enables a plurality of different frequencies of sound to be addressed.

Ideally, the tube or tubes have a spiral or helical configuration. This has been found to be a particularly effective way to maximize, or at least increase, the noise cancelling effect of the tubes while miniaturizing the device.

In a particularly preferred embodiment, the body of the device additionally comprises a second port into which sound can be played, and an audio communication route from the first port to the second port. This enables the patient to continue to hear the dentist while the device is reducing the volume of the drill. Alternatively, a personal music player such as an MP3 player can be connected directly to a second port in order that the patient can listen to music to calm their nerves while the dentist is operating the drill.

The second channel can connect the second port to the first channel.

DESCRIPTION OF THE PREFERRED EMBODIMENTS

Figure 1:
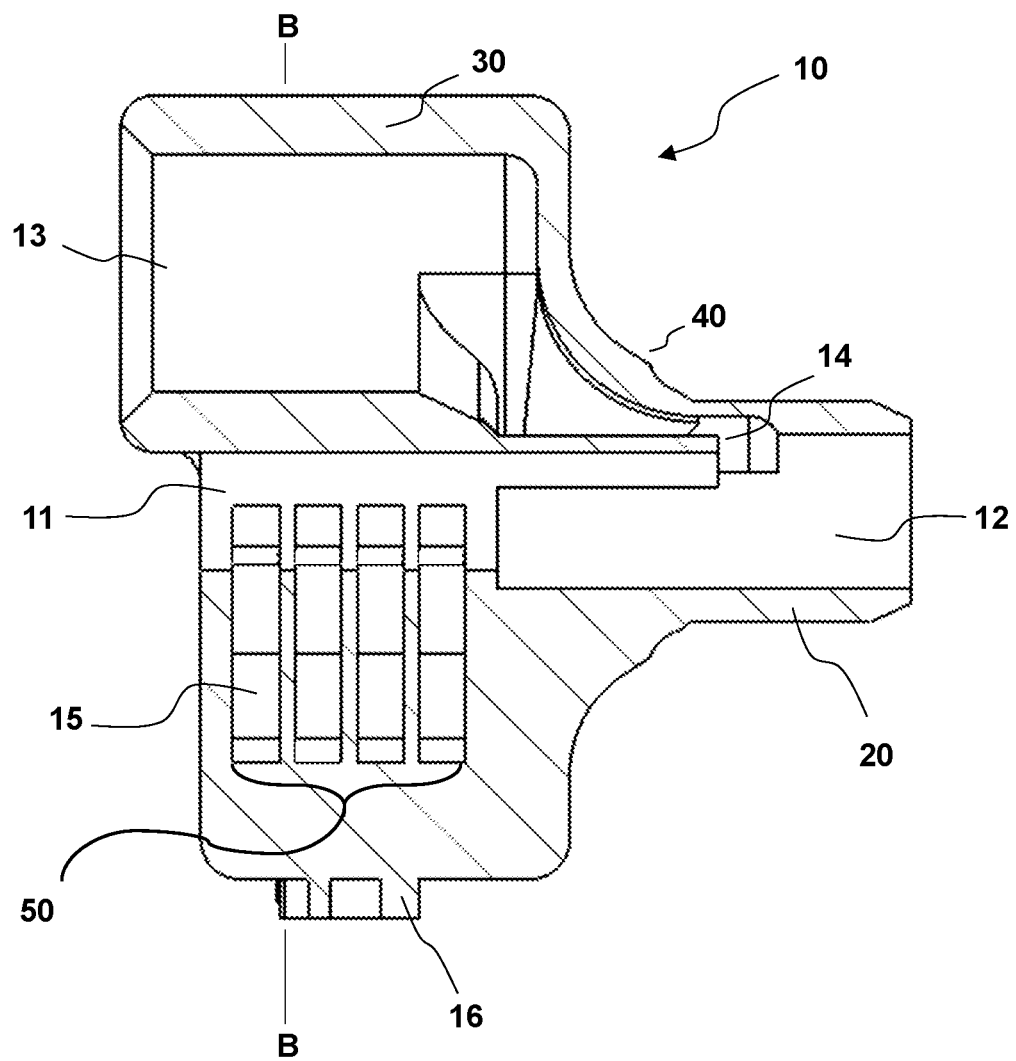
FIG. 1 shows a cross section through a noise cancellation device.

Turning to the figures, noise cancellation device 10 comprises cylindrical drum 30 of diameter 18.6 mm having cylindrical protrusion 20 of diameter 5.6 mm sharing a common longitudinal axis with and connected to drum 30 by curved shoulder 40. A channel is formed along the longitudinal axis of device 10 through drum 30 and protrusion 20 with the channel opening at vent 11 in the face of drum 30 and opening at port 12 in the face of protrusion 20. The internal diameter of this channel is about 3.00 mm at vent 11 and about 3.90 mm at port 12. It should be noted that noise cancellation device 10 is a laboratory model and is therefore larger in size than the envisaged production model of the device.

A further vent, namely music vent 13 is formed in the external face of drum 30 offset from vent 11 towards the periphery of drum 30. Music vent 13 forms a chamber internally in device 10 and then connects via music channel 14 with port 12. The version number is molded at 16.

Drum 30 also incorporates four layers 50 of resonator tubes 15, with five tubes 15 in each layer 50. In some embodiments three layers 50 are used. As can be seen from FIG. 3, resonator tubes 15 are in a spiral configuration with vent 11 at the center of each spiral and perpendicular to the plane of each layer 50. The resonator tubes are 1.6 mm or 2.00 mm wide by 1.15 mm deep and range in length from 8.5 mm to 19 mm.

Noise cancellation device 10 is used as follows:

Protrusion 20 is carefully fitted into the patient's external auditory canal so that port 12 aligns with the canal. It will be appreciated that shoulder 40 and drum 30 are shaped so as to prevent, or at least reduce the chance of, device 10 being pushed too far into the patient's canal and inadvertently causing damage.

External noise (such as the noise of a dentist's drill) passing through vent 11 has to pass through layers 50 of resonator tube 15 before exiting the device at port 12 and passing into the patient's ear canal. Layers 50 of resonator tubes 15 act as quarter-wave resonators and filter out frequencies of the drill. At the same time, they act as the low-pass filter to enable speech frequencies to pass through to the patient's ear, which means that the patient can still hear the dentist speaking.

If desired, the output from a personal musical player (such as an MP3 Player) can be fitted to music vent 13 in which case musical sound produced by this device bypasses the resonator tubes 15 via music channel 14 to pass through ports 12 into the patient's ear canal without being attenuated by device 10. Thus, the patient can listen to music while having the sound of the drill blocked out.

Example 1

Figure 5:
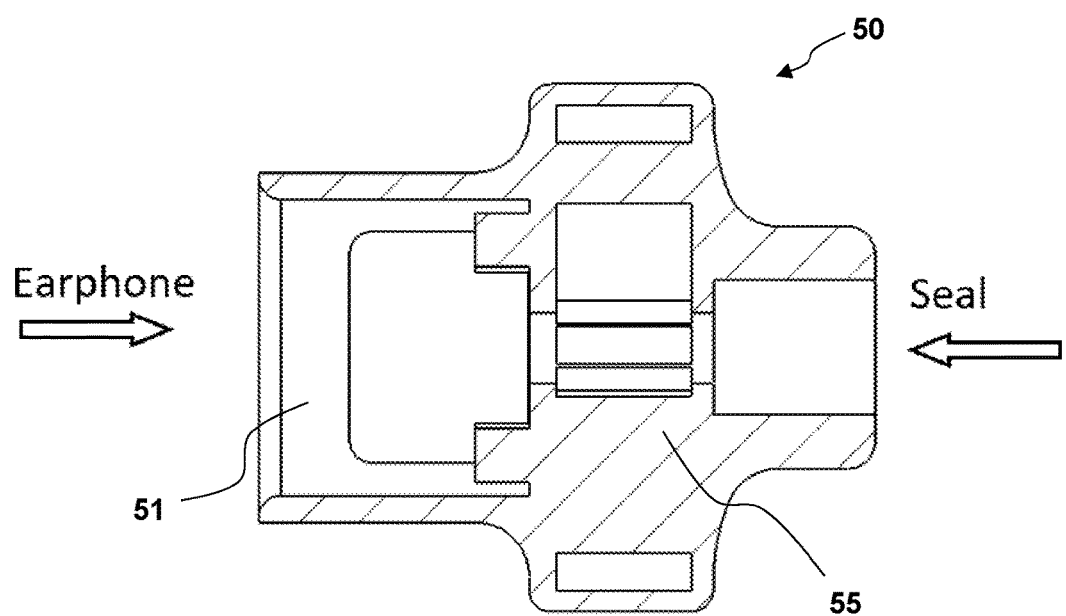
FIG. 5 is a cross-sectional view through B-B in FIG. 4, showing a device with a single layer of resonator tubes.
Figure 6:
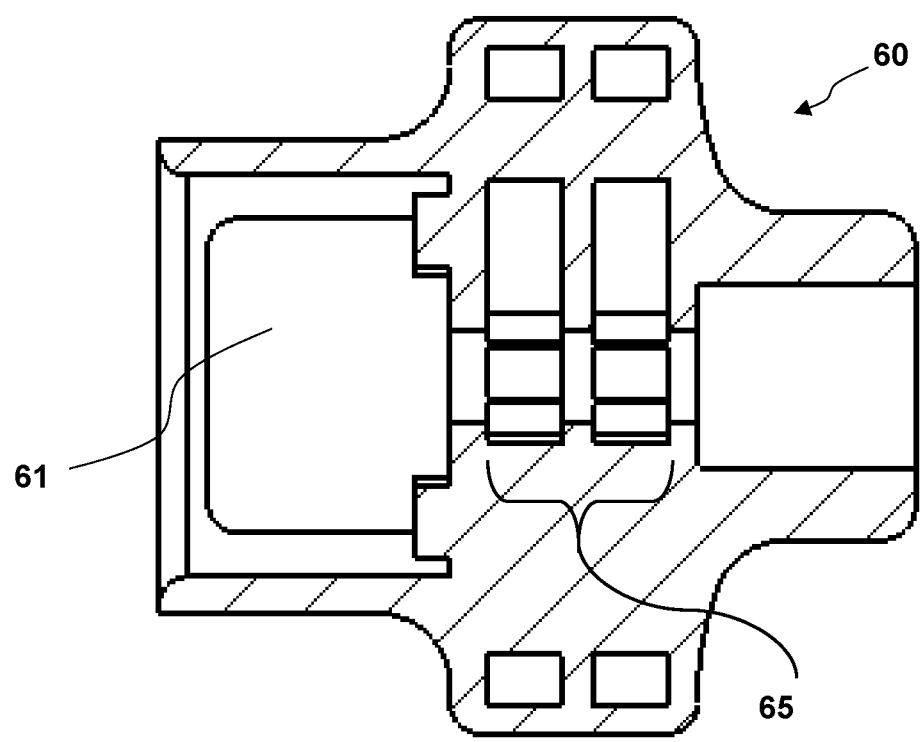
FIG. 6 is a cross-sectional view through B-B of an alternative device to that shown FIG. 4, showing a device with a double layer of resonator tubes.

Two devices were tested which were identical apart from the number of layers of resonator tubes. Device 50 shown in FIG. 5 had a single layer 55 5 mm wide of five resonator tubes and device 60, shown in FIG. 6, had a double layer 65 of five resonator tubes in each layer (each layer being 2.4 mm wide so that it fits in the same space as the single layer of FIG. 5). Both devices looked identical from the end view, as shown in FIG. 4.

The devices did not have a separate music vent or channel. Music could be played through the central vent 51, 61 along with the ambient sound.

Figure 4:
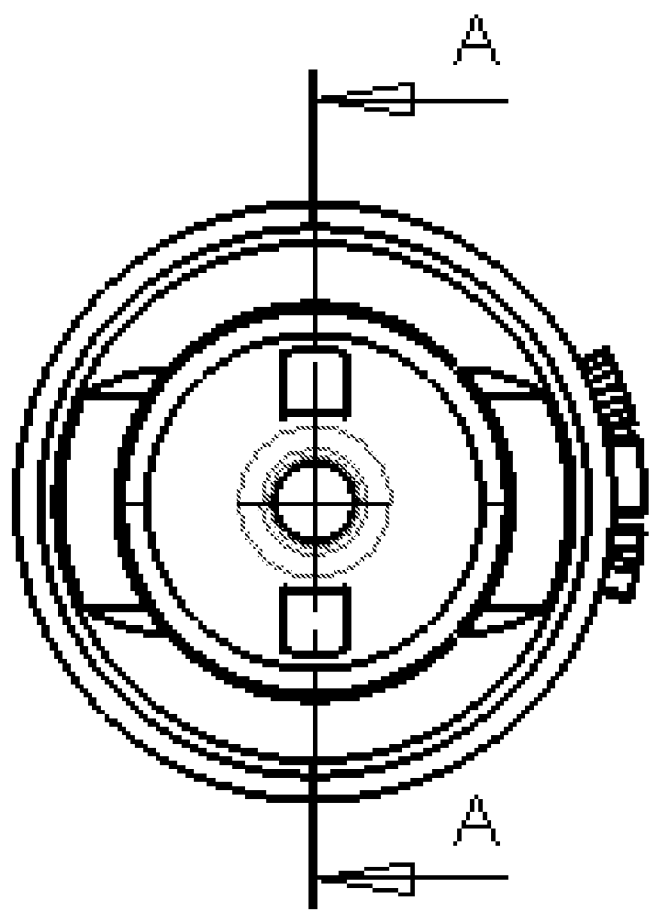
FIG. 4 is an end view of an alternative device.

Experimental Procedure (a) Each device was fitted with a 'fir tree' seal (also known as a 'polybud' and easily available from, for example, Canford Audio pic in the UK) and earphone (see FIG. 4).

(b) The device was located in a GRAS Ear and Cheek Simulator Type 43AG (ECS).

(c) White noise was played through a loudspeaker placed 150 mm from the device.

(d) The sound reaching the ECS microphone was recorded on a lab computer.

(e) The white noise was also recorded without a device in the ECS.

Figure 7:
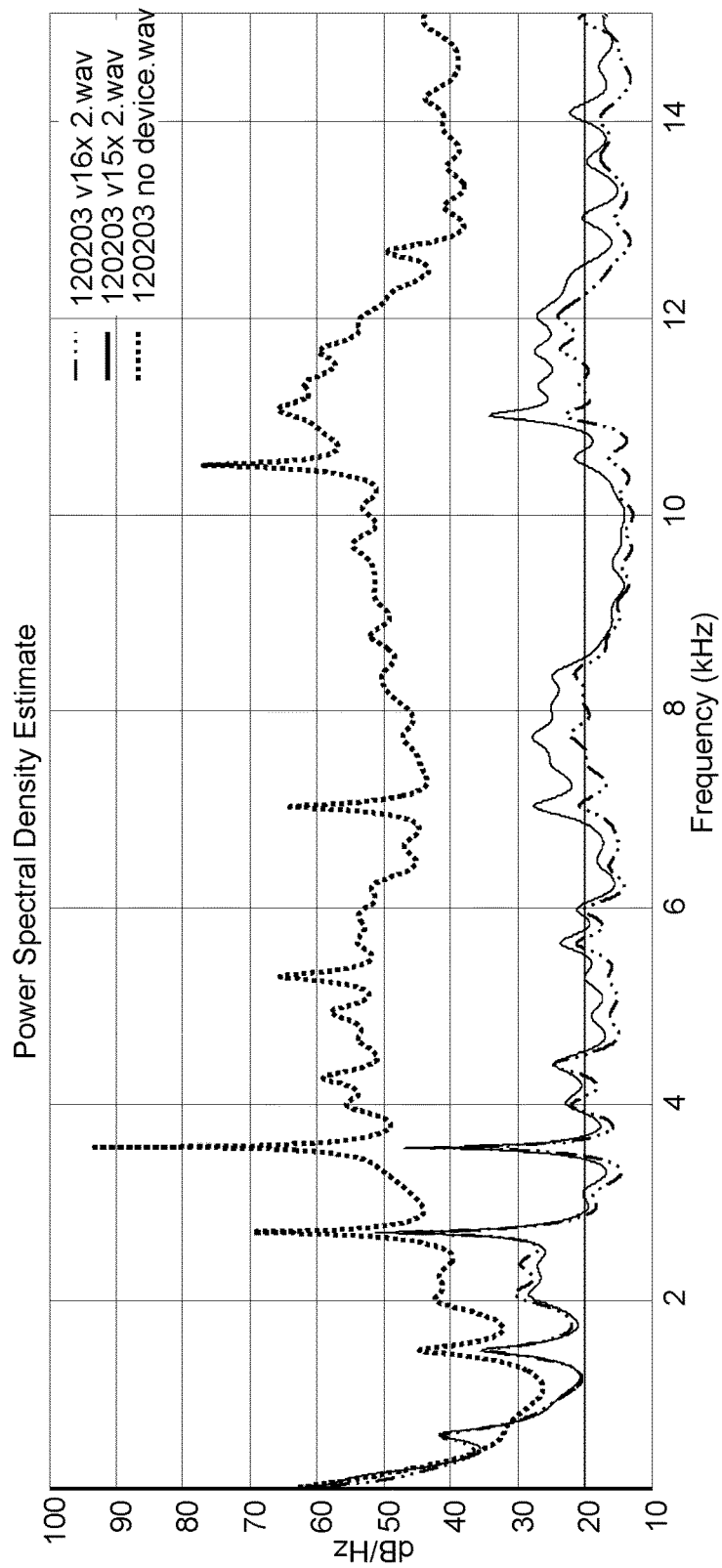
FIG. 7 is a graph of noise against frequency to demonstrate the noise-reducing effect of a 2-layer device compared to a 1-layer device.

(f) The sound recordings with and without devices were then plotted as sound pressure level against frequency using MATLAB (see FIG. 7).

FIG. 7 shows the greater noise reduction effect achieved with a 2-layer device (v16x) compared to a 1-layer device (v15x), particularly over 2.5 kHz. The 2-layer device reduces the white noise recorded with no device to a lower level than the 1-layer device (v15x).

Example 2

Figure 2:
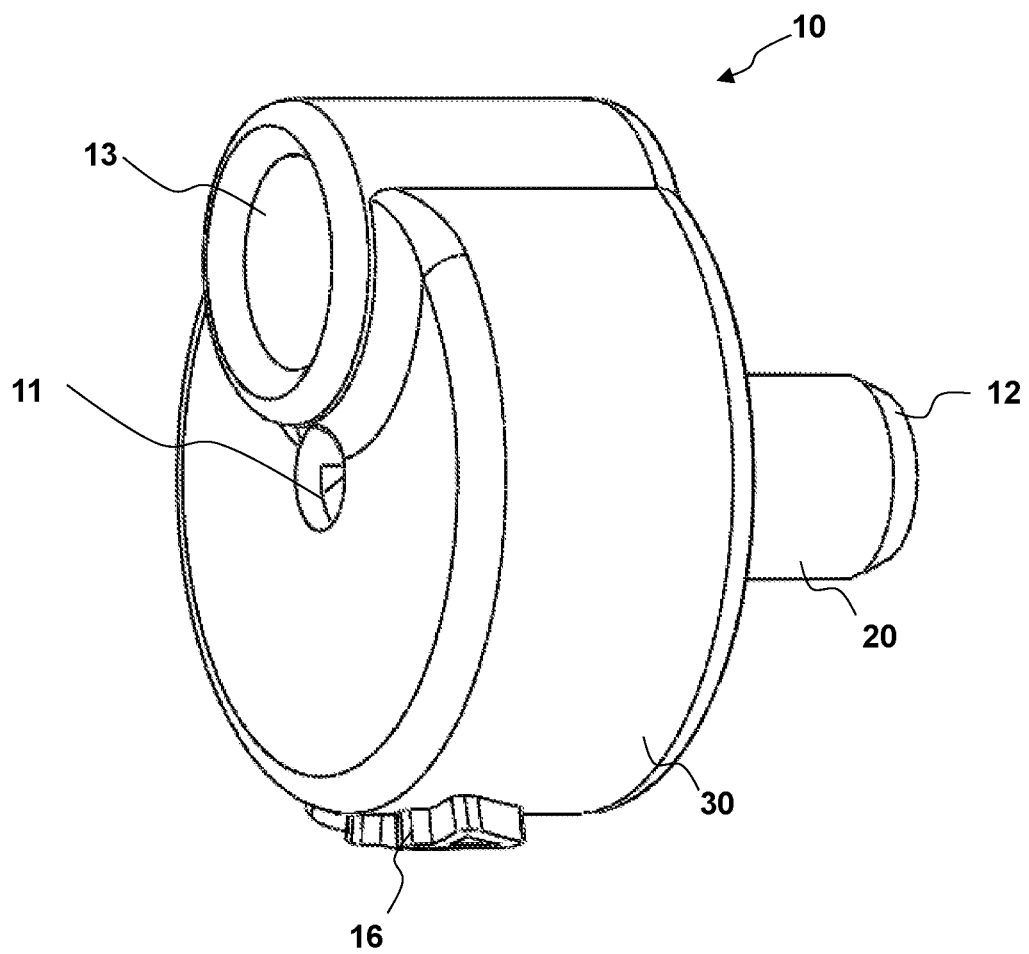
FIG. 2 is an external 3D render of a device as shown in FIG. 1.
Figure 3:
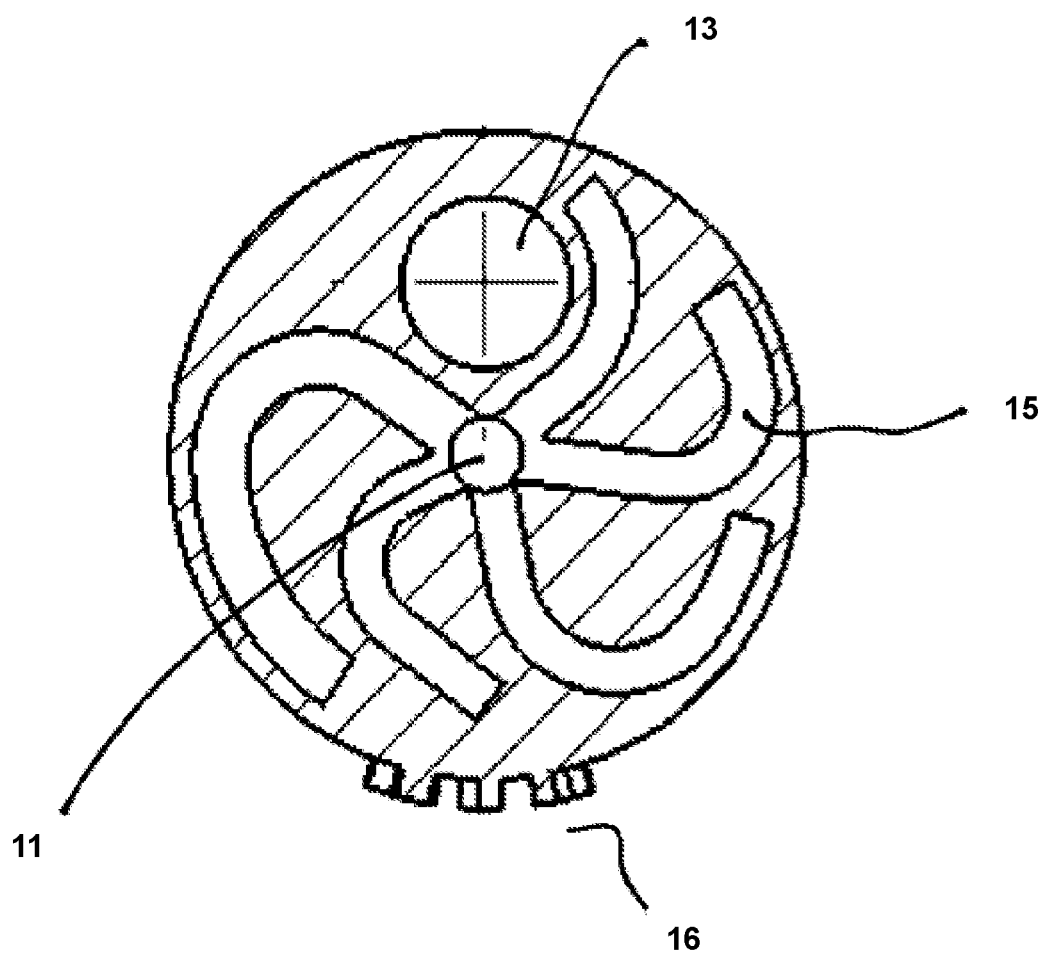
FIG. 3 is a schematic render of a cross section through B-B in FIG. 1.
Figure 8:
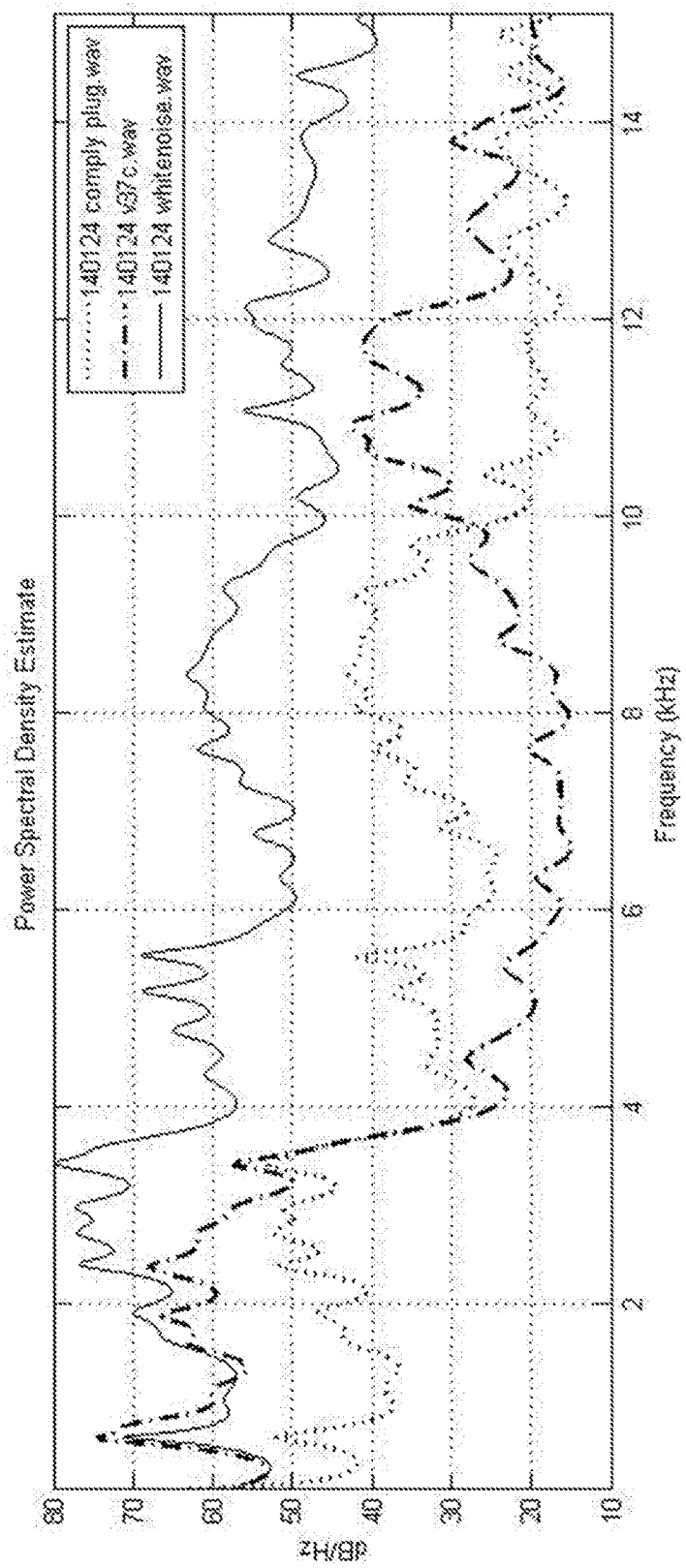
FIG. 8 is a graph of noise against frequency to demonstrate the noise-reducing effect of a device as shown in FIGS. 1 to 3 compared to a Comply™ foam plug.

The noise-reducing effect of a three layer device as shown in FIGS. 1-3 was compared to a Comply™ foam plug (marketed by Hearing Components, Inc. of Oakdale, Minn., US) by using the same experimental procedure as in Example 1 above. The results are shown in FIG. 8.

It can be seen that the device is more effective than the foam plug at reducing noise in the frequency range 4-10 kHz but leaves the (0-3.5 kHz) virtually unaffected.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. An in-ear device for use by a dental patient to reduce a perceived volume of a dental drill comprising:
   (i) a first port for communication with the external auditory canal of said patient's ear;
   (ii) a vent for communication with an external environment;
   (iii) a first channel connecting said first port and said vent; and
   (iv) a number of layers disposed in parallel planes, said number of layers comprising:
      (a) a number of resonator tubes disposed in a plane having a first end and a second end, wherein said first end is proximate to and in communication with said first channel and said second end is closed, and wherein said resonator tubes are curved along at least part of their longitudinal axis in order to reduce the length of a straight line from said first end to said second end, and wherein said number of resonator tubes are configured to function as quarter-wave resonators to reduce said perceived volume of said dental drill.

2. The device of claim 1 wherein said plane is normal to the longitudinal axis of said first channel.

3. The device of claim 1 wherein said number of layers is at least three.

4. The device of claim 1 wherein said number of resonator tubes in each said layer is independently between three and five.

5. The device of claim 4 wherein said number of resonator tubes is the same in each said layer.

6. The device of claim 1 wherein each of said resonator tubes are curved.

7. The device of claim 1 wherein at least two of said number of said resonator tubes have the same length as each other.

8. The device of claim 7 wherein said number of said layers further comprises:
   (b) a plurality of pairs of resonant tubes of the same length.

9. The device of claim 1 wherein at least one of said resonator tubes has a spiral or helical configuration.

10. The device of claim 1 further comprising:
   (v) a second port into which sound can be played; and
   (vi) an audio communication route from said first port to said second port.

11. The device of claim 10 further comprising:
   (vii) a second channel connecting said second port to said first channel.

12. A method of reducing the perceived volume of a tool by utilizing a device wherein said device comprises:
   (i) a first port for communication with the external auditory canal of said patient's ear;
   (ii) a vent for communication with an external environment;
   (iii) a first channel connecting said first port and said vent; and
   (iv) a number of layers disposed in parallel planes, said number of layers comprising:
      (a) a number of resonator tubes disposed in a plane having a first end and a second end, wherein said first end is proximate to and in communication with said first channel and said second end is closed, and wherein said resonator tubes are curved along at least part of their longitudinal axis in order to reduce the length of a straight line from said first end to said second end, and wherein said number of resonator tubes function as quarter-wave resonators to reduce said perceived volume of said dental drill.

13. An in-ear device for use by a dental patient to reduce a perceived volume of a dental drill comprising:
   (i) a first port for communication with the external auditory canal of said patient's ear;
   (ii) a vent for communication with an external environment;
   (iii) a first channel connecting said first port and said vent;
   (iv) a second port into which sound can be played;
   (v) an audio communication route from said first port to said second port; and
   (vi) three layers disposed in parallel planes, said three layers comprising:
      (a) a set of resonator tubes disposed in a plane normal to the longitudinal axis of said first channel, each of said resonator tubes of said set having a first end and a second end, wherein said first end is proximate to and in communication with said first channel and said second end is closed, and wherein each of said resonator tubes of said set are curved along at least part of their longitudinal axis in order to reduce the length of a straight line from said first end to said second end,
   wherein each of said resonator tubes of said set are quarter-wave resonators,
   wherein each of said resonator tubes of said set have the same length, and
   wherein each of said resonator tubes of said set have a helical configuration.

14. The device of claim 13 wherein a music player is connected to said second port.

* * * * *